(12) United States Patent
Park et al.

(10) Patent No.: US 11,654,416 B2
(45) Date of Patent: May 23, 2023

(54) METHOD FOR PREPARING SUPER-ABSORBENT POLYMER

(71) Applicant: LG Chem, Ltd., Seoul (KR)

(72) Inventors: Sung Soo Park, Daejeon (KR); Gi Cheul Kim, Daejeon (KR); Ju Eun Kim, Daejeon (KR); Hyeon Choi, Daejeon (KR); Hyo Sook Joo, Daejeon (KR); Sung Hyun Park, Daejeon (KR); Hee Jung Choi, Daejeon (KR); Ki Youl Yoon, Daejeon (KR)

(73) Assignee: LG Chem, Ltd.

( * ) Notice: Subject to any disclaimer, the term of this patent is extended or adjusted under 35 U.S.C. 154(b) by 287 days.

(21) Appl. No.: 17/193,601

(22) Filed: Mar. 5, 2021

(65) Prior Publication Data

US 2021/0187478 A1 Jun. 24, 2021

Related U.S. Application Data

(62) Division of application No. 15/524,697, filed as application No. PCT/KR2015/014428 on Dec. 29, 2015, now Pat. No. 10,981,146.

(30) Foreign Application Priority Data

Jan. 23, 2015 (KR) .................. 10-2015-0011037
Dec. 28, 2015 (KR) .................. 10-2015-0187758

(51) Int. Cl.
*B01J 20/26* (2006.01)
*C08J 3/075* (2006.01)
*C08J 3/12* (2006.01)
*C08K 9/06* (2006.01)
*C08J 3/24* (2006.01)
*B01J 20/28* (2006.01)
*B01J 20/10* (2006.01)
*B01J 20/30* (2006.01)
*B01J 20/32* (2006.01)
*A61F 13/53* (2006.01)

(52) U.S. Cl.
CPC .......... *B01J 20/267* (2013.01); *B01J 20/103* (2013.01); *B01J 20/265* (2013.01); *B01J 20/28004* (2013.01); *B01J 20/28007* (2013.01); *B01J 20/28011* (2013.01); *B01J 20/28059* (2013.01); *B01J 20/28061* (2013.01); *B01J 20/28064* (2013.01); *B01J 20/3021* (2013.01); *B01J 20/3085* (2013.01); *B01J 20/3204* (2013.01); *B01J 20/3282* (2013.01); *C08J 3/075* (2013.01); *C08J 3/12* (2013.01); *C08J 3/24* (2013.01); *C08J 3/245* (2013.01); *C08K 9/06* (2013.01); *A61F 2013/530481* (2013.01); *C08J 2300/14* (2013.01)

(58) Field of Classification Search
CPC ........ B01J 20/26; B01J 20/103; B01J 20/265; B01J 20/28004; B01J 20/28007; B01J 20/28011; B01J 20/28059; B01J 20/28061; B01J 20/28064; B01J 20/3021; B01J 20/3085; B01J 20/3204; B01J 20/3282; C08J 3/075; C08J 3/12; C08J 3/24; C08J 3/245; C08J 2300/14; C08K 9/06; A61F 2013/530481
USPC ......................................................... 502/402
See application file for complete search history.

(56) References Cited

U.S. PATENT DOCUMENTS

| | | |
|---|---|---|
| 5,032,628 A | 7/1991 | Choi et al. |
| 9,440,220 B2 | 9/2016 | Naumann et al. |
| 2002/0182377 A1 | 12/2002 | Morris et al. |
| 2003/0022081 A1 | 1/2003 | Inoue et al. |
| 2005/0070671 A1 | 3/2005 | Torii et al. |
| 2005/0096435 A1 | 5/2005 | Smith et al. |
| 2006/0073969 A1 | 4/2006 | Torii et al. |
| 2006/0204755 A1 | 9/2006 | Torii et al. |
| 2008/0058747 A1 | 3/2008 | Singh Kainth et al. |
| 2008/0075937 A1 | 3/2008 | Wada et al. |
| 2011/0224361 A1 | 9/2011 | Daniel et al. |
| 2012/0157622 A1 | 6/2012 | Lindner et al. |
| 2012/0157623 A1 | 6/2012 | Lindner et al. |
| 2012/0305842 A1 | 12/2012 | Torii et al. |
| 2013/0310251 A1 | 11/2013 | Smith et al. |

(Continued)

FOREIGN PATENT DOCUMENTS

| | | |
|---|---|---|
| CN | 1902265 A | 1/2007 |
| CN | 103260658 A | 8/2013 |

(Continued)

OTHER PUBLICATIONS

Extended European Search Report including Written Opinion for Application No. EP15879096.4 dated Apr. 24, 2018.
International Search Report for Application No. PCT/KR2015/014428 dated Apr. 1, 2016.
Odian, "Principles of Polymerization." Second Edition, Copyright 1981 by John Wiley & Sons, Inc., p. 203.

(Continued)

*Primary Examiner* — Edward M Johnson
(74) *Attorney, Agent, or Firm* — Lerner David LLP

(57) ABSTRACT

The present invention relates to a super-absorbent polymer having excellent properties, both centrifugal retention capacity (CRC) and absorption under pressure (AUP) having been improved by introducing a surface crosslinked layer crosslinked by surface-modified inorganic particles, and to a method for preparing the same. The super-absorbent polymer comprises: a base resin powder containing a crosslinked polymer of water-soluble ethylene-based unsaturated monomers having an at least partially neutralized acidic group; and a surface crosslinked layer formed on the base resin powder, wherein inorganic particles may be chemically bound to the crosslinked polymer contained in the surface crosslinked layer, via an oxygen-containing bond or a nitrogen-containing bond.

3 Claims, 3 Drawing Sheets

(56) References Cited

U.S. PATENT DOCUMENTS

| | | |
|---|---|---|
| 2015/0093575 A1 | 4/2015 | Naumann et al. |
| 2015/0246153 A1 | 9/2015 | Ota et al. |

FOREIGN PATENT DOCUMENTS

| | | | |
|---|---|---|---|
| JP | 2862357 | B2 | 3/1999 |
| JP | 2003064281 | A | 3/2003 |
| JP | 2008201134 | A | 9/2008 |
| JP | 4255233 | B2 | 4/2009 |
| JP | 2011074401 | A | 4/2011 |
| JP | 4739682 | B2 | 8/2011 |
| JP | 2012509377 | A | 4/2012 |
| JP | 5301159 | B2 | 9/2013 |
| JP | 2014500366 | A | 1/2014 |
| JP | 2014023766 | A | 2/2014 |
| JP | 2014504317 | A | 2/2014 |
| KR | 19910008293 | B1 | 10/1991 |
| KR | 20040058305 | A | 7/2004 |
| KR | 20070083761 | A | 8/2007 |
| KR | 20090042828 | A | 4/2009 |
| KR | 20120081113 | A | 7/2012 |
| KR | 20140102264 | A | 8/2014 |
| KR | 20140126821 | A | 11/2014 |

OTHER PUBLICATIONS

Schwalm, "UV Coatings: Basics, Recent Developments and New Applications." Elsevier Science, Dec. 21, 2006, p. 115.

[FIG. 1]
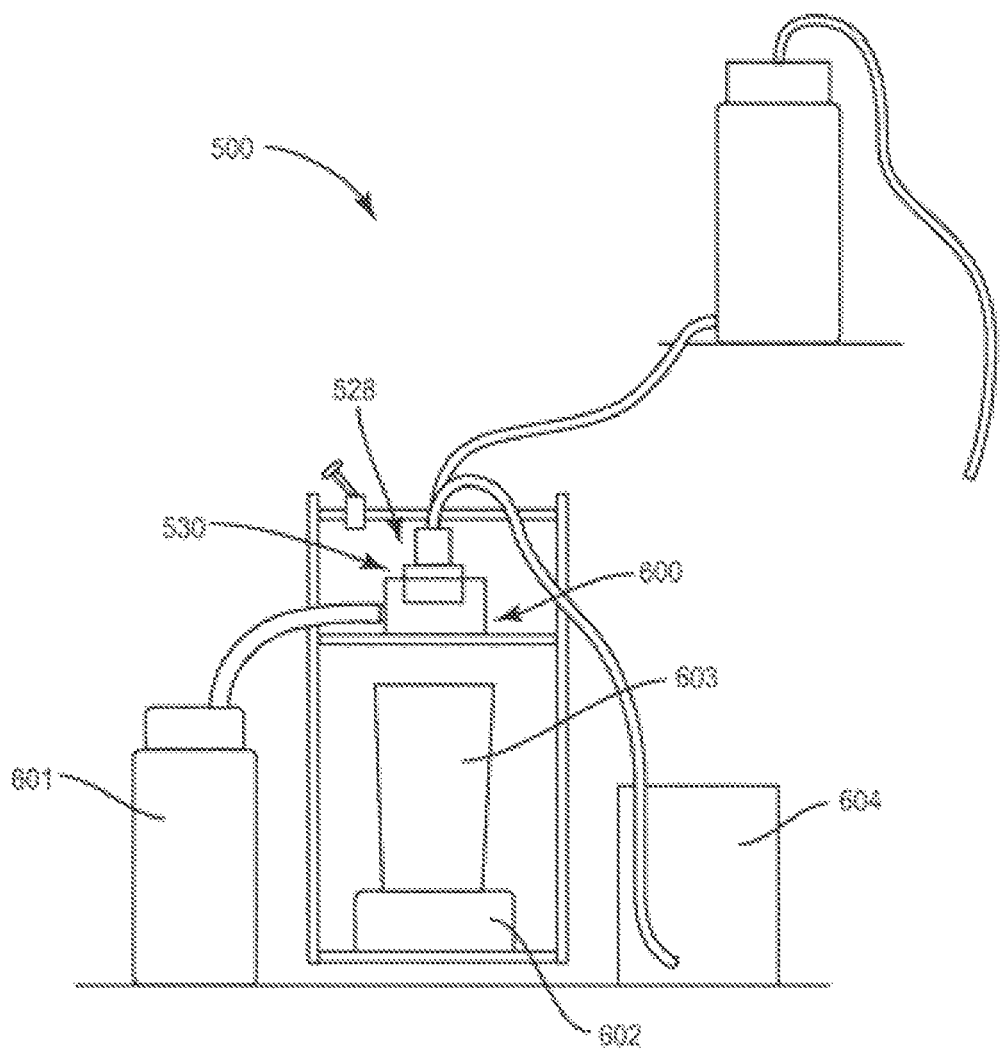

[FIG. 2]
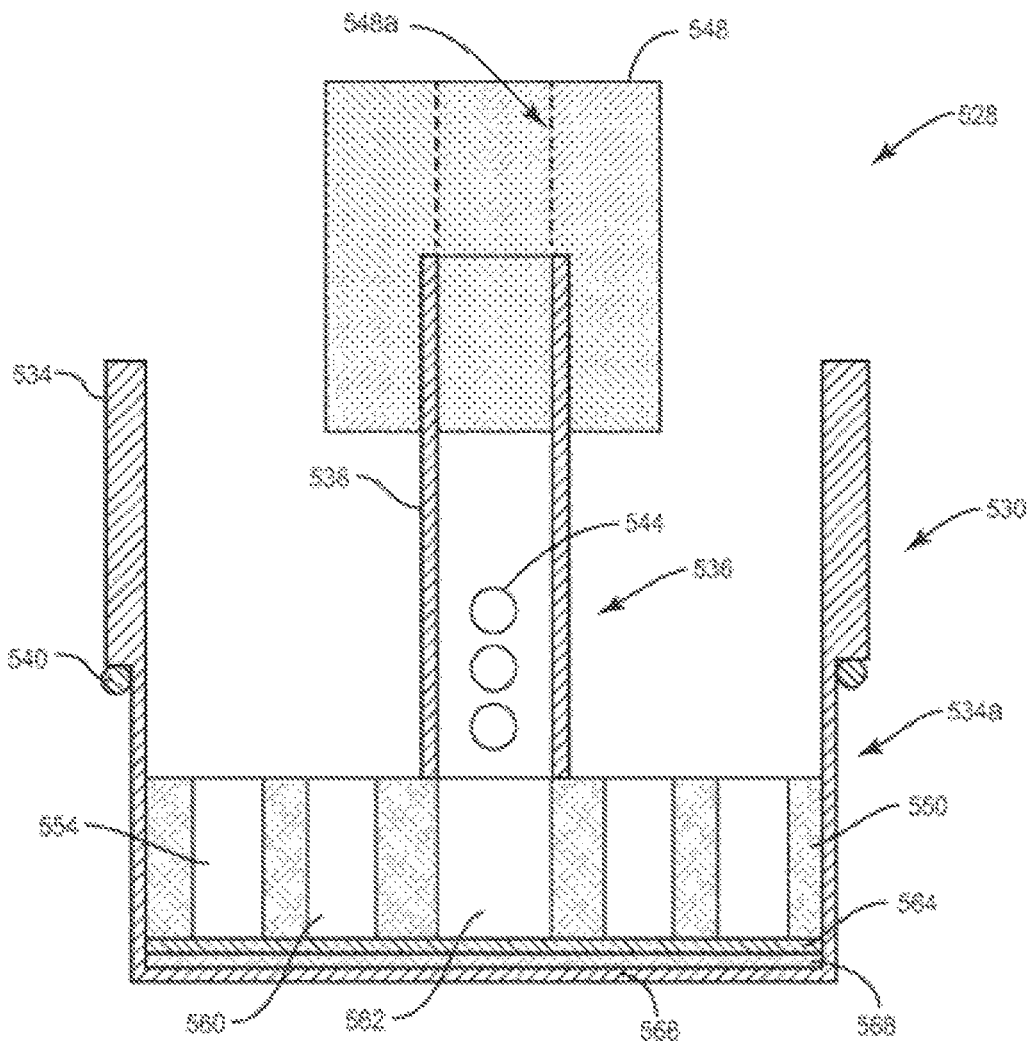

[FIG. 3]
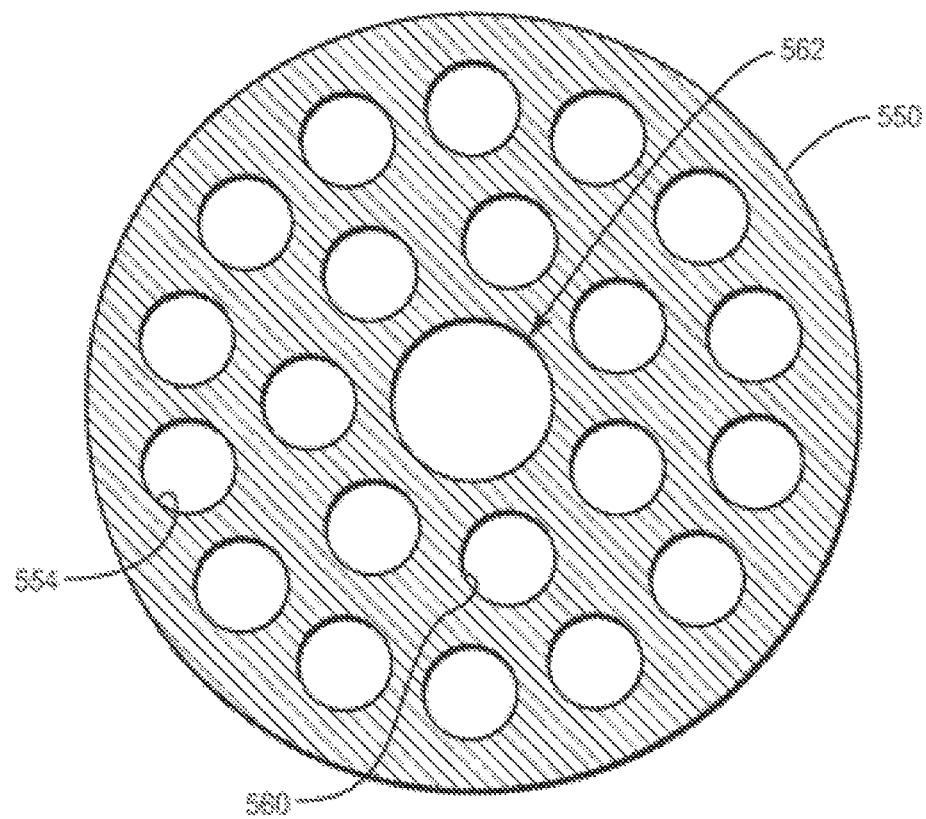

METHOD FOR PREPARING SUPER-ABSORBENT POLYMER

CROSS-REFERENCE TO RELATED APPLICATION

The present application is a divisional of U.S. application Ser. No. 15/524,697, filed on May 5, 2017, which is a national phase entry under 35 U.S.C. § 371 of International Application No. PCT/KR2015/014428, filed on Dec. 29, 2015, which claims the benefit of Korean Patent Application No. 10-2015-0011037, filed on Jan. 23, 2015, and Korean Patent Application No. 10-2015-0187758, filed on Dec. 28, 2015, with the Korean Intellectual Property Office, the disclosures of which are herein incorporated by reference in their entirety.

TECHNICAL FIELD

The present disclosure relates to a superabsorbent polymer, in which a surface crosslinking layer crosslinked by surface-modified inorganic particles is introduced, and therefore, centrifuge retention capacity (CRC), absorbency under pressure (AUP), and permeability are improved at the same time, and a preparation method thereof.

BACKGROUND ART

A super absorbent polymer (SAP) is a synthetic polymeric material capable of absorbing moisture in about 500 to 1000 times its own weight. Various manufacturers have been denominated it as different names such as SAM (Super Absorbency Material), AGM (Absorbent Gel Material) or the like. Since such superabsorbent polymers started to be practically applied in sanitary products, now they have been widely used not only for hygiene products such as disposable diapers for children, sanitary napkins etc., but also for water retaining soil products for gardening, water stop materials for the civil engineering and construction, sheets for raising seedling, fresh-keeping agents for food distribution fields, materials for poultice or the like.

In many cases, such superabsorbent polymers are widely used in hygiene products such as diapers, sanitary napkins etc. For this purpose, superabsorbent polymers are required to have high water absorption, must not release absorbed water even under an external pressure, and also must maintain the shape under volume expansion (swelling) due to water absorption to show excellent permeability.

Reportedly, it is difficult to improve centrifuge retention capacity (CRC), which is a basic physical property of showing water absorption and retention capacities, and absorbency under pressure (AUP), which is a property of retaining absorbed water even under an external pressure, at the same time. The reason is that when the overall crosslinking density of the superabsorbent polymer is controlled to be low, centrifuge retention capacity becomes relatively high, but a crosslinking structure becomes loose and gel strength becomes low, leading to a reduction in absorbency under pressure. On the contrary, when the crosslinking density is controlled to be high, and therefore absorbency under pressure is improved, water is hardly absorbed between compact crosslinking structures, leading to a reduction in basic centrifuge retention capacity. Because of the above-described reasons, there have been limitations in the preparation of superabsorbent polymers having both improved centrifuge retention capacity and absorbency under pressure.

Meanwhile, when superabsorbent polymers are exposed to high humidity, superabsorbent polymers absorb water in air and agglomerate together into a large mass, that is, a caking phenomenon occurs. To prevent this caking phenomenon, superabsorbent polymers are mixed with an inorganic additive such as silica.

However, effective dispersion of the inorganic additive in the superabsorbent polymer is difficult, and therefore, the effect of the inorganic additive is unsatisfactory. Further, because of physical blending of the inorganic additive with the superabsorbent polymer, the inorganic additive breaks away therefrom to cause problems of dust generation and changes in physical properties.

DISCLOSURE

Technical Problem

Accordingly, the present invention is intended to provide a superabsorbent polymer, of which surface is crosslinked by surface-modified inorganic particles, thereby having excellent physical properties of showing improved centrifuge retention capacity (CRC), absorbency under pressure (AUP), and permeability at the same time.

Further, the present invention is intended to provide a method of preparing the superabsorbent polymer.

Technical Solution

The present disclosure provides a superabsorbent polymer including a base polymer powder including a crosslinked polymer resulting from polymerization of water-soluble ethylene-based unsaturated monomers having acidic groups which are at least partially neutralized, in the presence of an internal crosslinking agent; and a surface crosslinking layer formed on the base polymer by additionally crosslinking the crosslinked polymer in the presence of surface-modified inorganic particles, in which inorganic particles chemically bind to the crosslinked polymer included in the surface crosslinking layer via an oxygen-containing bond or a nitrogen-containing bond.

Further, the present invention provides a method of preparing the superabsorbent polymer, the method including the steps of: performing crosslinking polymerization of water-soluble ethylene-based unsaturated monomers having acidic groups which are at least partially neutralized, in the presence of an internal crosslinking agent to form a hydrogel polymer; drying, pulverizing, and classifying the hydrogel polymer to form the base polymer powder; and additionally crosslinking the surface of the base polymer powder in the presence of inorganic particles which are surface-modified with one or more functional groups selected from the group consisting of an epoxy group, a hydroxy group, an isocyanate group, and an amine group to form the surface crosslinking layer.

Hereinafter, the superabsorbent polymer and the preparation method thereof will be described in more detail according to specific embodiments of the present invention. However, these are for illustrative purposes only, and the scope of the present invention is not intended to be limited thereby. It will be apparent to those skilled in the art that various modifications may be made thereto without departing from the scope of the invention.

Additionally, the term "including" or "containing" means that it includes a particular component (or particular element) without particular limitations unless otherwise mentioned in the present entire disclosure, and it cannot be interpreted as it excludes the addition of the other components.

According to an embodiment of the present invention, provided is the superabsorbent polymer including the base polymer powder including the crosslinked polymer resulting from polymerization of water-soluble ethylene-based unsaturated monomers having acidic groups which are at least partially neutralized, in the presence of an internal crosslinking agent; and the surface crosslinking layer formed on the base polymer by additionally crosslinking the crosslinked polymer in the presence of surface-modified inorganic particles, in which inorganic particles chemically bind to the crosslinked polymer included in the surface crosslinking layer via an oxygen-containing bond or a nitrogen-containing bond.

The experimental results of the present inventors demonstrated that when the surface crosslinking layer is formed by additionally crosslinking the surface of the base polymer powder in the presence of inorganic particles surface-modified with one or more functional groups selected from the group consisting of an epoxy group, a hydroxy group, an isocyanate group, and an amine group, the inorganic particles chemically bind to the crosslinked polymer included in the surface crosslinking layer, and therefore, breakaway of the inorganic particles from the superabsorbent polymer may be prevented during preparation and transportation of the superabsorbent polymer, and the superabsorbent polymer may have improved absorbency under pressure and permeability, thereby completing the present invention.

The superabsorbent polymer thus prepared includes, for example, the base polymer powder including the crosslinked polymer which is formed by crosslinking polymer chains of the water-soluble ethylene-based unsaturated monomers via a crosslinkable functional group of the internal crosslinking agent, and the surface crosslinking layer formed by additionally crosslinking the crosslinked polymers present on the surface of the base polymer powder with inorganic particles which are surface-modified by two or more crosslinkable functional groups per one particle.

Accordingly, the superabsorbent polymer of an embodiment has the surface crosslinking layer which is formed by crosslinking the crosslinked polymers present on the surface via surface-modified inorganic particles, and has a structure in which the crosslinked polymers in the surface crosslinking layer chemically bind with inorganic particles through an oxygen-containing bond or a nitrogen-containing bond derived from crosslinkable functional groups of the inorganic particles. More particularly, the crosslinked polymers in the surface crosslinking layer chemically bind with the inorganic particles through an oxygen-containing bond such as —O—, —COO—, etc. or a nitrogen-containing bond such as —CONR— or —NR— (R is hydrogen or an alkyl group having 1 to 3 carbon atoms).

Owing to the surface crosslinking structure including the inorganic particles, agglomeration between particles hardly occurs, thereby effectively preventing a caking phenomenon in the superabsorbent polymer of an embodiment, that is, agglomeration of particles into a large mass due to absorption of water in air by the superabsorbent polymer. Further, the inorganic particles occupy a predetermined space between the surface crosslinking structures. For this reason, the superabsorbent polymer may exhibit an improved water absorption rate, and may also exhibit excellent permeability by maintaining the shape under volume expansion (swelling) upon absorbing water. Particularly, owing to the above-described novel surface crosslinking structure, the superabsorbent polymer may exhibit superior characteristics of being excellent in both centrifuge retention capacity and absorbency under pressure, unlike the known inverse relationship between centrifuge retention capacity and absorbency under pressure. Consequently, the superabsorbent polymer of an embodiment may exhibit superior physical properties by solving the problems of the existing superabsorbent polymers and satisfying a technical demand in the related art.

Hereinafter, the structure of the superabsorbent polymer of an embodiment and the preparation method thereof will be described in more detail.

Basically, the superabsorbent polymer of an embodiment includes the crosslinked polymers formed by crosslinking polymerization of the water-soluble ethylene-based unsaturated monomers as a base polymer powder and the surface crosslinking layer formed on the base polymer powder, like the previous superabsorbent polymers.

Additionally, in the superabsorbent polymer of an embodiment, the inorganic particles chemically bind (e.g., a covalent bond or a crosslinking bond, etc.) to the polymer chains of the crosslinked polymers present on the surface of the base polymer powder via an oxygen-containing bond or a nitrogen-containing bond derived from the crosslinkable functional group by using the above-described surface-modified inorganic particles as a crosslinkable functional group during surface crosslinking of the crosslinked polymer and the base polymer powder. Therefore, overall physical properties as described above may be improved (in particular, centrifuge retention capacity and absorbency under pressure may be improved at the same time).

With regard to the superabsorbent polymer of an embodiment, as the water-soluble ethylene-based unsaturated monomer, one or more selected from the group consisting of an anionic monomer such as acrylic acid, (meth)acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth) acrylamide-2-methyl propane sulfonic acid, and salts thereof; a nonionic hydrophilic monomer such as (meth) acrylamide, N-substituted (meth)acrylamide, 2-hydroxyethyl(meth)acrylate, 2-hydroxypropyl(meth)acrylate, methoxy polyethylene glycol (meth)acrylate, or polyethylene glycol (meth)acrylate; and an amino group-containing unsaturated monomer such as (N,N)-dimethylaminoethyl (meth)acrylate or (N,N)-dimethylaminopropyl(meth)acrylamide, and a quaternary compound thereof may be used. Among them, acrylic acid or salts thereof, for example, acrylic acid which is at least partially neutralized and/or alkali metal salts such as sodium salts thereof may be used, and it is possible to prepare a superabsorbent polymer having superior physical properties by using these monomers. When the alkali metal salt of acrylic acid is used as the monomer, acrylic acid may be used after neutralized with a basic compound such as caustic soda (NaOH). In this regard, the degree of neutralization of the water-soluble ethylene-based unsaturated monomer may be controlled in the range of about 50% to about 95%, or about 70% to about 85%. When neutralization is performed within the above range, it is possible to provide superabsorbent polymer having excellent centrifuge retention capacity without concerns about precipitation.

Further, as the internal crosslinking agent for introduction of the basic crosslinking structure into the crosslinked polymer and the base polymer powder, any internal crosslinking agent having a crosslinkable functional group which has been previously used in the preparation of the superabsorbent polymer may be used without particular limitation. In order to further improve physical properties of the superabsorbent polymer by introducing a proper crosslinking structure into the crosslinked polymer and the base polymer powder, however, a multifunctional acrylate-based compound having a plurality of ethylene oxide groups may be used as the internal crosslinking agent. More specific examples of the internal crosslinking agent may be one or more selected from the group consisting of polyethylene glycol diacrylate (PEGDA), glycerin diacrylate, glycerin triacrylate, non-modified or ethoxylated trimethylolpropane triacrylate (TMPTA), hexanediol diacrylate, and triethylene glycol diacrylate.

Further, in the superabsorbent polymer of an embodiment, the surface-modified inorganic particles for the preparation of the surface crosslinking layer on the base polymer powder may be inorganic particles surface-modified with the above-described crosslinkable functional group.

The inorganic particles may have a specific surface area of 5 m$^2$/g to 600 m$^2$/g or 100 m$^2$/g to 300 m$^2$/g. Within this range, the inorganic particles may be surface-modified with an appropriate number of the crosslinkable functional groups. The inorganic particles has a diameter of 5 to 500 nm, and thus an appropriate number of the inorganic particles based on the same weight may be dispersed well in the surface crosslinking layer, which is economical.

More specifically, the inorganic particles may be silica particles, alumina particles, etc.

Further, the above-described inorganic particles may be bound in an amount of about 0.01 to about 2 parts by weight, based on 100 parts by weight of the superabsorbent polymer. Consequently, a crosslinking structure including an appropriate amount of the inorganic particles is introduced into the surface crosslinking layer, and therefore, the superabsorbent polymer of an embodiment may have more improved physical properties, for example, centrifuge retention capacity and absorbency under pressure. Meanwhile, a more specific kind of the surface-modified inorganic particles and a preparation method thereof are provided for reference in the aftermentioned preparation method.

In the superabsorbent polymer of an embodiment, the surface crosslinking layer formed on the base polymer powder may be formed by using a surface crosslinking agent which has been previously used in the preparation of the superabsorbent polymer, together with the surface-modified inorganic particles. As the surface crosslinking agent, any surface crosslinking agent known in the art to which the present invention pertains may be used without particular limitation. A more specific example thereof may be one or more selected from the group consisting of ethylene glycol, 1,4-butanediol, 1,6-hexanediol, propylene glycol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, glycerol, ethylene carbonate and propylene carbonate.

The above-described superabsorbent polymer of an embodiment may exhibit characteristics that centrifuge retention capacity (CRC) for a physiological saline solution is about 30 g/g to about 40 g/g, absorbency under pressure (AUP) of 0.7 psi for the physiological saline solution is about 10 g/g to about 26 g/g or about 20 g/g to about 26 g/g, and free swell gel bed permeability (GBP) is about 5 darcy to about 120 darcy or about 9 darcy to about 120 darcy.

The above-described superabsorbent polymer of an embodiment may exhibit excellent centrifuge retention capacity, together with more improved permeability and absorbency under pressure, by introducing the surface crosslinking structure including inorganic particles into the surface crosslinking layer. Accordingly, the superabsorbent polymer is preferably applied to a variety of hygiene products such as diapers, etc., thereby exhibiting very excellent physical properties.

Meanwhile, the centrifuge retention capacity (CRC) for a physiological saline solution may be measured according to EDANA WSP 241.2. More specifically, the centrifuge retention capacity may be calculated by the following Equation 1, after the superabsorbent polymer is immersed in the physiological saline solution for 30 minutes:

$$CRC(g/g)=\{[W2(g)-W1(g)]/W0(g)\}-1 \quad \text{[Equation 1]}$$

wherein W0(g) is the initial weight (g) of the superabsorbent polymer, W1(g) is the weight of an empty bag which is measured after immersing the empty bag in the physiological saline solution at room temperature for 30 minutes and draining water off at 250 G for 3 minutes with a centrifuge, and W2(g) is the weight of the bag including the superabsorbent polymer, which is measured after immersing the bag including the superabsorbent polymer in the physiological saline solution at room temperature for 30 minutes and draining water off at 250 G for 3 minutes with a centrifuge.

The absorbency under pressure (AUP) of 0.7 psi may be measured according to EDANA WSP 242. More specifically, the absorbency under pressure may be calculated by the following Equation 2, after immersing the superabsorbent polymer in the physiological saline solution under a pressure of about 0.7 psi for 1 hour:

$$AUP(g/g)=[W4(g)-W3(g)]/W0(g) \quad \text{[Equation 2]}$$

wherein W0(g) is the initial weight (g) of the superabsorbent polymer, W3(g) is the total weight of the superabsorbent polymer and an apparatus capable of providing a load for the superabsorbent polymer, and W4(g) is the total weight of the superabsorbent polymer and the apparatus capable of providing a load for the superabsorbent polymer, which are measured after immersing the superabsorbent polymer in the physiological saline solution under a load of about 0.7 psi for 1 hour.

W0(g) in Equations 1 to 2 may be, corresponding to the initial weight (g) of the superabsorbent polymer before immersing the superabsorbent polymer in the physiological saline solution, the same as or different from each other.

The gel bed permeability (GBP) for the physiological saline solution may be measured as a unit of Darcy or cm$^2$ according to a method described in Patent Application No. 2014-7018005. 1 Darcy means a flow of 1 mm per 1 sec of a fluid with a viscosity 1 cP under a pressure gradient of 1 atm per 1 cm acting across an area of 1 cm$^2$. Gel bed permeability has the same units as area, and 1 darcy is equal to $0.98692 \times 10^{-12}$ m$^2$ or $0.98692 \times 10^{-8}$ cm$^2$.

More specifically, in this specification, GBP means permeability of a swollen gel layer (or bed) under free swell conditions of 0 psi (Gel Bed Permeability (GBP) Under 0 psi Swell Pressure Test), and GBP may be measured by an apparatus shown in FIGS. 1 to 3.

Referring to FIGS. 1 to 3, in an apparatus 500 for measuring GBP, a test apparatus assembly 528 includes a sample container 530 and a plunger 536. The plunger includes a shaft 538 having a cylinder hole bored down the longitudinal axis and a head 550 positioned at the bottom of the shaft. The shaft hole 562 has a diameter of about 16 mm. The plunger head is attached to the shaft, for example, by an adhesive. Twelve holes 544 are bored into the radial axis of the shaft, and three holes positioned at every 90 degrees have diameters of about 6.4 mm. The shaft 538 is machined from a LEXAN rod or equivalent material and has an outer diameter of about 2.2 cm and an inner diameter of about 16 mm. The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but may be machined at the top of the shaft to obtain the desired mass of the plunger 536. The plunger 536 includes a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent. The sample container 530 includes a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent. A gel particle sample (swollen superabsorbent polymer), indicated by 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of about 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 may be made from stainless steel or from other suitable materials resistant to corrosion in the presence of 0.9% by weight of a physiological saline solution (sodium chloride solution). The combined weight of the plunger 536 and annular weight 548 equals approximately 596 g, which corresponds to a pressure applied to the sample 568 of about 0.3 psi, or about 20.7 dyne/cm$^2$ (2.07 kPa), over a sample area of about 28.27 cm$^2$.

When the test solution flows through the test apparatus during GBP testing, the sample container 530 generally rests on a weir 600. The purpose of the weir is to divert liquid that overflows the top of the sample container 530 and diverts the overflow liquid to a separate collection device 601. The weir may be positioned above a scale 602 with a beaker 603 resting on it to collect the physiological saline solution passing through the swollen sample 568.

To conduct the gel bed permeability test under "free swell" conditions, the plunger 536, with the weight 548 seated thereon, is placed in an empty sample container 530, and the height from the top of the weight 548 to the bottom of the sample container 530 is measured using a suitable gauge accurate to 0.01 mm. The force the thickness gauge applies during measurement should be as low as possible, preferably less than about 0.74 N. When a multiple test apparatus is used, it is important to measure the height of each sample container 530 empty and to keep track of which plunger 536 and weight 248 are used.

Desirably, the base on which the sample container 530 is placed is flat, and the top surface of the weight 548 is parallel to the bottom surface of the sample container 530. The sample to be tested for GBP is prepared from a superabsorbent polymer, for example, which is prescreened through a US standard 30 mesh screen and retained on a US standard 50 mesh screen. As a result, a superabsorbent polymer having a diameter of about 300 μm to about 600 μm is prepared as the test sample. Approximately 2.0 g of the sample is placed in the sample container 530 and spread out evenly on the bottom of the sample container. The container, with 2.0 g of sample in it, without the plunger 536 and weight 548 therein, is then submerged in the 0.9% by weight of physiological saline solution for about 60 minutes to allow the sample to swell free of any restraining load. In this regard, the sample container 530 is set on a mesh located in the liquid reservoir so that the sample container 530 is raised slightly above the bottom of the liquid reservoir. The mesh does not inhibit the flow of the physiological saline solution into the sample container 530. A suitable mesh may be obtained as part number 7308 from Eagle Supply and Plastic (having a place of business in Appleton, Wis., USA). Also, depth of the physiological saline solution during saturation may be controlled so that the surface within the sample container is defined solely by the sample, rather than the physiological saline solution. At the end of this period, the plunger 536 and weight 548 assembly is placed on the saturated sample 568 in the sample container 530, and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The plate will prevent liquid in the sample container from being released onto a flat surface due to surface tension. The plate has an overall dimension of 7.6 cm×7.6 cm, and each grid has a size dimension of 1.59 cm long×1.59 cm wide×1.12 cm deep. A suitable plate material is a parabolic diffuser panel, catalogue number 1624K27, available from McMaster Carr Supply Company (having a place of business in Chicago, Ill., USA), which may then be cut to the proper dimensions.

The height from the top of the weight 548 to the bottom of the sample container 530 is measured again using the same thickness gauge used previously, provided that the zero point is unchanged from the initial height measurement. The height measurement should be made as soon as practicable after the thickness gauge is engaged. The height measurement obtained from measuring the empty assembly where the plunger 536 and the weight 548 are placed in the empty sample container 530 is subtracted from the height measurement obtained after saturating the sample 568. The resulting value is the thickness, or height "H" of the saturated sample 568. Further, if the plate is included in the assembly including the saturated sample 568, the plate must also be present when measuring the height of the empty assembly.

The GBP measurement is initiated by delivering a flow of the 0.9% physiological saline solution into the sample container 530 with the saturated sample 568, plunger 536, and weight 548 inside. The flow rate of the physiological saline solution into the container is adjusted to cause saline solution to overflow the top of the cylinder 534, resulting in a consistent head pressure equal to the height of the sample container 530. The physiological saline solution may be added by any suitable means that is sufficient to ensure a small, but consistent amount of overflow from the top of the cylinder with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q through the swollen sample 568 is determined in units of g/sec by a linear least-square fit of fluid (g) passing through the sample 568 versus time (sec).

Data thus obtained are used to calculate GBP ($cm^2$) according to the following Equation 3, thereby obtaining gel bed permeability.

$K=[Q*H*\mu]/[A*\rho*P]$ [Equation 3]

wherein K is a gel bed permeability ($cm^2$),
Q is a flow rate (g/sec),
H is a height of the swollen sample (cm),
$\mu$ is a liquid viscosity (P) (approximately 1 cP for the test solution used in this test),
A is a cross-sectional area for liquid flow (28.27 $cm^2$ for the sample container used in this test),
$\rho$ is a liquid density (g/$cm^3$) (approximately 1 g/$cm^3$ for the test solution used in this test) and
P is a hydrostatic pressure (dyne/$cm^2$) (normally approximately 7,797 dyne/$cm^2$).

The hydrostatic pressure is calculated from $P=\rho*g*h$, wherein $\rho$ is a liquid density (g/$cm^3$), g is a gravitational acceleration (nominally 981 cm/$sec^2$), and h is a fluid height (e.g., 7.95 cm for the GBP test described herein).

The above-described superabsorbent polymer of an embodiment may be a spherical or amorphous particle having a diameter of about 150 μm to about 850 μm.

Meanwhile, according to another embodiment of the present invention, provided is a method of preparing the above-described superabsorbent polymer. The method of preparing the superabsorbent polymer may include the steps of performing crosslinking polymerization of water-soluble ethylene-based unsaturated monomers having acidic groups which are at least partially neutralized, in the presence of an internal crosslinking agent to form a hydrogel polymer; drying, pulverizing, and classifying the hydrogel polymer to form the base polymer powder; and additionally crosslinking the surface of the base polymer powder in the presence of inorganic particles surface-modified with one or more functional groups selected from the group consisting of an epoxy group, a hydroxy group, an isocyanate group, and an amine group to form the surface crosslinking layer.

In the preparation method of another embodiment, crosslinking polymerization of water-soluble ethylene-based unsaturated monomers is performed in the presence of an internal crosslinking agent, and the resulting polymer is dried, pulverized, and classified to form the base polymer powder according to a general preparation method of the superabsorbent polymer. Thereafter, unlike the previous methods, the surface of the base polymer powder is additionally crosslinked using inorganic particles, which are surface-modified with crosslinkable functional groups such as an epoxy group, a hydroxy group, an isocyanate group, and an amine group, to prepare the superabsorbent polymer.

That is, in the preparation method of another embodiment, the superabsorbent polymer may be prepared according to the general preparation method, except that the surface-modified inorganic particles are used upon surface crosslinking, and therefore, the surface-modified inorganic particles and a preparation method thereof will be first described, and then each step of the method of preparing the superabsorbent polymer using the same will be briefly described.

The surface-modified inorganic particles may be prepared by reacting a surface modifier having a crosslinkable functional group and inorganic particles such as silica particles or alumina particles. In this regard, a specific example of the surface modifier may be a compound represented by the following Chemical Formula 1:

[Chemical Formula 1]

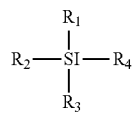

wherein $R_1$ to $R_3$ are each independently an alkyl group having 1 to 10 carbon atoms, an alkoxy group having 1 to 10 carbon atoms, or halogen, and at least one of them is not an alkyl group, and $R_4$ is a substituent having 2 to 10 carbon atoms, which has one or more functional groups selected from the group consisting of an epoxy group, a hydroxy group, an isocyanate group, and an amine group.

With regard to the surface-modified inorganic particles, it is desirable that the inorganic particles are surface-modified by introducing about 2 to about 200, or about 10 to about 150, or about 20 to about 100 crosslinkable functional groups into one inorganic particle. Consequently, an appropriate crosslinking structure may be introduced into the superabsorbent polymer finally prepared by the above preparation method. Considering the appropriate number of the crosslinkable functional groups introduced into one inorganic particle, the inorganic particles and the surface modifier are reacted in a proper appropriate to prepare the surface-modified inorganic particles.

More specifically, the inorganic particles may be exemplified by silica particles such as fumed silica or colloidal silica. Of them, when fumed silica is used, the inorganic particle and the surface modifier may be reacted so that the surface of the silica particle is modified with the crosslinkable functional group at a ratio of about 0.008 umol/$m^2$ to about 0.8 umol/$m^2$, or about 0.04 umol/$m^2$ to about 0.4 umol/$m^2$, based on 1 $m^2$ of the surface area of the silica particle. When colloidal silica is used, the inorganic particle and the surface modifier may be reacted so that the surface of the silica particle is modified with the crosslinkable functional group at a ratio of about 0.014 umol/$m^2$ to about 1.4 umol/$m^2$, or about 0.07 umol/$m^2$ to about 0.7 umol/$m^2$, based on 1 $m^2$ of the surface area of the silica particle.

In the preparation method of another embodiment, crosslinking polymerization of water-soluble ethylene-based unsaturated monomers having acidic groups which are at least partially neutralized is first performed in the presence of an internal crosslinking agent to form the hydrogel polymer.

In this regard, the kind and the structure of the internal crosslinking agent and the water-soluble ethylene-based unsaturated monomer are the same as described above, and additional descriptions thereof will be omitted.

In a monomer composition including the water-soluble ethylene-based unsaturated monomer and the internal cross-linking agent, the concentration of the water-soluble ethylene-based unsaturated monomer may be about 20% by weight to about 60% by weight or about 40% by weight to about 50% by weight, based on the total weight of the monomer composition including the above described raw materials and solvent, and properly controlled in consideration of polymerization time and reaction conditions. However, if the concentration of the monomer is too low, the yield of the superabsorbent polymer may become low, and thus an economical problem may occur. On the contrary, if the concentration of the monomer is too high, there is a process problem that a part of the monomers is precipitated, or pulverization efficiency is lowered upon pulverization of the polymerized hydrogel polymer, and the physical properties of the superabsorbent polymer may be deteriorated.

Further, the monomer composition may further include a polymerization initiator which is generally used in the preparation of the superabsorbent polymer.

Specifically, the polymerization initiator may be a thermal polymerization initiator or a photo-polymerization initiator by UV irradiation, depending on a polymerization method. However, even though the photo-polymerization is performed, a certain amount of heat may be generated by UV irradiation or the like, and also generated with exothermic polymerization reaction. Therefore, the thermal polymerization initiator may be further included.

As the photo-polymerization initiator, a compound capable of forming radicals by a light such as UV may be used without limitations in the constitution.

For example, as the photo-polymerization initiator, one or more selected from the group consisting of benzoin ether, dialkyl acetophenone, hydroxyl alkylketone, phenyl glyoxylate, benzyl dimethyl ketal, acyl phosphine, and α-aminoketone may be used. Of them, acyl phosphine may be used as the photo-polymerization initiator. The acyl phosphine may be diphenyl(2,4,6-trimethylbenzoyl)phosphine oxide, phenylbis(2,4,6-trimethyl benzoyl)phosphine oxide, ethyl(2,4,6-trimethylbenzoyl)phenylphosphinate, etc. More various photo-polymerization initiators are well disclosed in "UV Coatings: Basics, Recent Developments and New Application (Elsevier, 2007)" written by Reinhold Schwalm, p 115, however, they are not limited to the above described examples.

The concentration of the photo-polymerization initiator may be about 0.001% by weight to about 1.0% by weight, based on the total weight of the monomer composition. If the concentration of the photo-polymerization initiator is too low, the polymerization rate may become low. If the concentration of the photo-polymerization initiator is too high, the molecular weight of the superabsorbent polymer may become low and its physical properties may be not uniform.

Further, as the thermal polymerization initiator, one or more selected from the group consisting of persulfate-based initiators, azo-based initiators, hydrogen peroxide, and ascorbic acid may be used. Specific examples of the persulfate-based initiators may include sodium persulfate ($Na_2S_2O_8$), potassium persulfate ($K_2S_2O_8$), ammonium persulfate (($NH_4)_2S_2O_8$) or the like. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis(2-[2-imidazolin-2-yl]propane)dihydrochloride, 4,4-azobis-(4-cyanovaleric acid) or the like. More various thermal polymerization initiators are well-disclosed in 'Principle of Polymerization (Wiley, 1981)' written by Odian, p 203, however, they are not limited to the above described examples.

The concentration of the thermal polymerization initiator may be about 0.001% by weight to about 0.5% by weight, based on the total weight of the monomer composition. If the concentration of the thermal polymerization initiator is too low, additional thermal polymerization hardly occurs, and thus the addition effect of the thermal polymerization initiator may not be sufficiently obtained. If the concentration of the thermal polymerization initiator is too high, the molecular weight of the superabsorbent polymer may become low and the content of water-soluble components is increased, thereby deteriorating absorbency under pressure of a final superabsorbent polymer product.

The kind of the internal crosslinking agent included in the monomer composition is the same as described above, and the internal crosslinking agent may be included in an amount of about 0.01% by weight to about 0.5% by weight, based on the monomer composition, thereby crosslinking the polymerized polymer. In particular, when the internal crosslinking agent is used in an amount of about 0.3 parts by weight or more, or about 0.3 parts by weight to about 0.6 parts by weight, based on 100 parts by weight of the above-described monomer, for example, non-neutralized acrylic acid, it is possible to prepare a superabsorbent polymer which more properly satisfies the above described physical properties of an embodiment.

The monomer composition may further include an additive such as a thickener, a plasticizer, a preservation stabilizer, an antioxidant, etc., if necessary.

The raw materials such as the above-described water-soluble ethylene-based unsaturated monomer, photo-polymerization initiator, thermal polymerization initiator, internal crosslinking agent, and additive may be prepared in the form of a solution of the monomer composition which is dissolved in a solvent.

In this regard, as the solvent, any solvent may be used without limitations in the constitution as long as it is able to dissolve the above ingredients, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate and N,N-dimethylacetamide may be used in combination.

The solvent may be included in a residual amount of excluding the above described components from the total weight of the monomer composition.

Meanwhile, as long as the method for forming the hydrogel polymer by thermal polymerization or photo-polymerization of the monomer composition is a method generally used, there is no particular limitation in the constitution.

Specifically, the polymerization method is largely classified into the thermal polymerization and the photo-polymerization according to the polymerization energy source. The thermal polymerization may be carried out in a reactor like a kneader equipped with agitating spindles, and the photo-polymerization may be carried out in a reactor equipped with a movable conveyor belt. The above-described polymerization method is an example only, and the present invention is not limited thereto.

For example, thermal polymerization of the monomer composition may be performed by providing hot air for a reactor like a kneader equipped with the agitating spindles or heating the reactor. The hydrogel polymer thus obtained by thermal polymerization may have the size of centimeters or millimeters when it is discharged from the outlet of the reactor, according to the type of agitating spindles equipped in the reactor. Specifically, the hydrogel polymer may be obtained in various forms according to the concentration of the monomer composition fed thereto, the feeding speed or the like, and the hydrogel polymer having a weight average particle size of about 2 mm to about 50 mm may be generally obtained.

Further, as described above, when the photo-polymerization is carried out in a reactor equipped with a movable conveyor belt, the hydrogel polymer generally obtained may be a hydrogel polymer in a sheet-type having a width of the belt. In this regard, the thickness of the polymer sheet may vary according to the concentration of the monomer composition fed thereto and the feeding speed, and the feeding speed of the monomer composition is preferably controlled so that the polymer sheet having a thickness of about 0.5 cm to about 5 cm is obtained. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the polymer due to the excessively high thickness.

A light source to be used in the photo-polymerization method is not particularly limited, and a non-limiting example thereof may be a light source such as a Xe lamp, a mercury lamp, a metal halide lamp, etc.

Meanwhile, the monomer composition may be thermally polymerized after it is photo-polymerized. In this case, a reactor capable of providing a movable conveyor belt, a UV light source, and hot air may be used, and photo-polymerization and thermal polymerization may be sequentially performed.

The hydrogel polymer thus obtained by the method may have generally a water content of about 40% by weight to about 80% by weight. Meanwhile, the term "water content", as used herein, means a water content in the total weight of the hydrogel polymer, which is obtained by subtracting the weight of the dry polymer from the weight of the hydrogel polymer. Specifically, the water content is defined as a value calculated by measuring the weight loss according to evaporation of water in the polymer during the drying process of increasing the temperature of the polymer with infrared heating. In this regard, the water content is measured under the drying conditions which are determined as follows; the temperature is increased from room temperature to about 180° C. and then the temperature is maintained at 180° C., and the total drying time is determined as 20 minutes, including 5 minutes for the temperature rising step.

After crosslinking polymerization of the monomer, drying, pulverizing, and classifying processes may be performed to obtain the base polymer powder. Through the pulverizing and classifying processes, the base polymer powder and the superabsorbent polymer obtained therefrom are properly prepared to have a particle size of about 150 μm to about 850 μm. More specifically, about 95% by weight or more of the base polymer powder and the superabsorbent polymer obtained therefrom have a particle size of about 150 μm to 850 μm, and the content of fine powder having a particle size of less than about 150 μm may be less than about 3% by weight.

As the particle size distributions of the base polymer powder and the superabsorbent polymer are controlled within the preferred range, the final superabsorbent polymer may exhibit the above-described physical properties and more excellent permeability.

Meanwhile, the drying, pulverizing, and classifying processes are described in more detail as follows.

First, in the process of drying the hydrogel polymer, the step of coarsely pulverizing the hydrogel polymer may be performed before the drying process, in order to increase efficiency of the drying process, if necessary.

In this regard, a pulverizing device applicable may include, but the constitution is not limited, any one selected from the group consisting of a vertical pulverizer, a turbo cutter, a turbo grinder, a rotary cutter mill, a cutter mill, a disc mill, a shred crusher, a crusher, a chopper, and a disc cutter, but is not limited thereto.

In this regard, the coarse pulverization may be performed so that the hydrogel polymer has a particle size of about 2 mm to about 10 mm.

To pulverize the hydrogel polymer at a particle size of less than 2 mm is technically not easy due to its high water content, and agglomeration may occur between the pulverized particles. If the hydrogel polymer is pulverized at a particle size of more than 10 mm, the effect of increasing the efficiency in the subsequent drying step may become insignificant.

The hydrogel polymer coarsely pulverized as above or immediately after polymerization without the coarse pulverization is subjected to a drying process. In this regard, the drying temperature of the drying step may be about 100° C. to about 250° C.

When the drying temperature is lower than 100° C., the drying time becomes excessively long or the physical properties of the superabsorbent polymer finally formed may be deteriorated, and when the drying temperature is higher than 250° C., only the surface of the polymer is dried, and thus fine powder may be generated during the subsequent pulverization process, and the physical properties of the superabsorbent polymer finally formed may be deteriorated.

Any known drying method may be selected and used in the drying step without limitation in the constitution as long as it may be generally used for drying the hydrogel polymer. Specifically, the drying step may be carried out by a method of supplying hot air, irradiating infrared rays, irradiating microwaves, irradiating ultraviolet rays or the like. When the drying step as above is finished, the water content of the polymer may be about 0.1% by weight to about 10% by weight.

Next, the dried polymer obtained from the drying step is subjected to a pulverization step.

The polymer powder obtained from the pulverization step may have a particle size of about 150 μm to about 850 μm. A specific example of a milling device which may be used to pulverize the polymer within the above particle size range may include a pin mill, a hammer mill, a screw mill, a roll mill, a disc mill, a jog mill or the like, but the present invention is not limited thereto.

In order to manage the physical properties of the superabsorbent polymer powder finally manufactured after the pulverization step, the polymer powder obtained after the pulverization may be subjected to an additional classifying step according to the particle size. Only a polymer having a particle size of about 150 μm to about 850 μm is preferably classified and then selectively applied to the surface crosslinking reaction, and finally manufactured. The particle size distribution of the base polymer powder obtained through this process is as described above, and a specific description thereof will be omitted.

Meanwhile, after the process of forming the above-described base polymer powder, the surface of the base polymer powder is additionally crosslinked in the presence of the surface-modified inorganic particles to form the surface crosslinking layer, thereby finally preparing the superabsorbent polymer.

In this regard, the kind and structure of the surface-modified inorganic particles are as described above, and additional descriptions thereof will be omitted.

The surface-modified inorganic particles may be used in an amount of 0.01 to 10 parts by weight, 0.01 to 5 parts by weight or 0.01 to 3 parts by weight, based on 100 parts by weight of the base polymer powder. When the surface-modified inorganic particles are used within the above range, the superabsorbent polymer having excellent centrifuge retention capacity and absorbency under pressure and improved permeability may be prepared.

Further, for a proper surface crosslinking density of the surface crosslinking layer, a surface crosslinking agent generally used in the surface crosslinking of the superabsorbent polymer may be used, together with the surface-modified inorganic particles. The kind of the surface crosslinking agent is as described above, and an additional description thereof will be omitted.

In the surface crosslinking process, the surface crosslinking reaction is performed by adding polyvalent metal cations, together with the surface-modified inorganic particles, thereby further optimizing the surface crosslinking structure of the superabsorbent polymer. It is assumed that the metal cations are chelated by the carboxylic groups (COOH) of the superabsorbent polymer, thereby further reducing the crosslinking distance.

With regard to the method of adding the surface-modified inorganic particles to the base polymer powder, there is no limitation in the constitution. For example, a method of adding and mixing the surface-modified inorganic particles and the base polymer powder in a reactor, a method of spraying the surface-modified inorganic particles onto the base polymer powder, or a method of continuously feeding the base polymer powder and the surface-modified inorganic particles to a mixer which is continuously operated may be used.

When the surface-modified inorganic particles are added, a mixture of water and methanol may be further added. When water and methanol are added, there is an advantage that the surface-modified inorganic particles are uniformly dispersed in the base polymer powder. In this regard, the contents of water and methanol added may be properly controlled, in order to induce uniform dispersion of the surface-modified inorganic particles, to prevent agglomeration of the base polymer powder, and to optimize the surface penetration depth of the inorganic particles.

The surface-modified inorganic particles are added to the base polymer powder, and then they may be heated at about 100° C. to about 200° C. for about 1 minute to about 120 minutes to allow the surface crosslinking reaction. More specifically, the surface crosslinking reaction may be allowed for about 1 minute to about 120 minutes, about 5 minutes to about 100 minutes, or about 10 minutes to about 80 minutes, after temperature reaches the target temperature for the reaction. If the crosslinking reaction time is excessively shorter than the above, sufficient surface crosslinking reaction may not occur. If the crosslinking reaction time is excessively long, the physical properties of the superabsorbent polymer may be deteriorated due to excessive surface crosslinking reaction, and degradation of the superabsorbent polymer may occur due to long retention of the polymer in the reactor.

A means for raising the temperature for surface crosslinking reaction is not particularly limited. Heating may be performed by providing a heating medium or by directly providing a heat source. In this regard, the type of the heating medium applicable may be a hot fluid such as steam, hot air, hot oil, or the like. However, the present invention is not limited thereto. The temperature of the heating medium provided may be properly controlled, considering the means of the heating medium, the heating rate, and the target temperature. Meanwhile, as the heat source provided directly, an electric heater or a gas heater may be used, but the present invention is not limited to these examples.

The superabsorbent polymer obtained according to the above-described preparation method may exhibit excellent characteristics of having improved physical properties such as centrifuge retention capacity and absorbency under pressure, thereby being properly applied to hygiene products such as diapers, etc.

Effect of the Invention

According to the present invention, provided are a superabsorbent polymer and a preparation method thereof, in which the superabsorbent polymer may exhibit superior characteristics of being excellent in both centrifuge retention capacity and absorbency under pressure, unlike the known inverse relationship between centrifuge retention capacity and absorbency under pressure.

Consequently, the superabsorbent polymer of the present invention may exhibit superior physical properties by solving the problems of the existing superabsorbent polymers and satisfying a technical demand in the related art, thereby being very preferably applied to a variety of hygiene products.

BRIEF DESCRIPTION OF DRAWINGS

FIGS. 1 to 3 illustrate an exemplary apparatus for measuring gel bed permeability and components equipped in the apparatus.

DETAILED DESCRIPTION OF THE EMBODIMENTS

Hereinafter, the preferred Examples are provided for better understanding. However, the following Examples are for illustrative purposes only, and the present invention is not intended to be limited by following Examples.

Preparation Example 1: Preparation of Surface-Modified Inorganic Particles (Introduction of Epoxy Group)

5% by weight of Aerosil 200 (Evonik) was dispersed in water to prepare 100 g of a solution. Subsequently, 1 mL of acetic acid was added to this solution to adjust pH to 3. Then, 2 g of (3-(glycidyloxy)propyl)trimethoxysilane was added thereto. To the solution thus obtained, 70 g of 1 mm bead ($ZrO_2$) was added, and mixed for about 24 hours to modify the surface of the inorganic particles. A product thus obtained was washed with n-butyl acetate to obtain surface-modified inorganic particles.

Preparation Example 2: Preparation of Surface-Modified Inorganic Particles (Introduction of Epoxy Group)

200 g of IPA (iso-propyl alcohol) and 12 g of (3-(glycidyloxy)propyl)trimethoxysilane were added to 100 g of Ludox HSA (silica content: 30% by weight). To the solution thus obtained, 70 g of 1 mm bead ($ZrO_2$) was added, and mixed for about 24 hours to modify the surface of the inorganic particles. A product thus obtained was washed with n-butyl acetate to obtain surface-modified inorganic particles.

(Ludox HSA is colloidal silica having a particle size of 12 nm and a specific surface area of 215 $m^2/g$)

Example 1: Preparation of Superabsorbent Polymer 100 g of acrylic acid, 38.9 g of caustic soda (NaOH), and 103.9 g of water were mixed. To this mixture, 0.01 g of a photo-polymerization initiator, diphenyl(2,4,6-trimethylbenzoyl)phosphine oxide, 0.18 g of a thermal polymerization initiator, sodium persulfate, and 0.35 g of an internal crosslinking agent, polyethylene glycol diacrylate were added to prepare a monomer composition. Temperature of the monomer composition was maintained at 40° C. in a water bath.

Meanwhile, for photo-polymerization and thermal polymerization of the monomer composition, used was an apparatus which was equipped with a biaxial rotary silicon belt and a mercury lamp placed on the belt and was able to provide hot air for an insulated space after UV irradiation.

The monomer composition of which temperature was controlled in the water bath was fed to the belt of the apparatus. The monomer composition on the belt was irradiated with UV at an intensity of 10 mW for 60 seconds using the mercury lamp placed on the top of the belt. After UV irradiation, hot air was provided for the photo-polymerized polymer to maintain temperature at 90° C. for thermal polymerization. Thereafter, a hydrogel polymer discharged through a cutter was dried in a hot air dryer at 180° C. for 1 hour.

The hydrogel polymer thus dried was pulverized using a pin mill pulverizer. Thereafter, the polymer was classified into a polymer having a particle size of less than about 150 μm and a polymer having a particle size of about 150 μm to about 850 μm using a sieve.

Thereafter, a surface treatment solution including 1.0 part by weight of 1,3-propanediol, 1 part by weight of water, and 0.1 part by weight of the surface-modified inorganic particles prepared in Preparation Example 1, based on 100 parts by weight of the prepared base polymer powder, was sprayed and stirred at room temperature to uniformly distribute the surface crosslinking agent and the surface treatment solution in the base polymer powder.

Thereafter, the mixture was fed to a surface crosslinking reactor set at about 180° C. to allow surface crosslinking reaction. In the surface crosslinking reactor, the temperature of the base polymer powder was gradually increased from the initial temperature near about 160° C., and reached a maximum temperature of about 180° C. after about 30 minutes. After reaching the maximum reaction temperature, additional reaction was allowed for about 20 minutes, thereby obtaining a final superabsorbent polymer sample. After the surface crosslinking process, a surface-crosslinked superabsorbent polymer having a particle size of about 150 μm to about 850 μm was obtained by using a sieve. The content of fine powder having a particle size of about 150 μm or less in the superabsorbent polymer was less than about 2% by weight.

Example 2: Preparation of Superabsorbent Polymer

A superabsorbent polymer was prepared in the same manner as in Example 1, except that 0.3 parts by weight of the surface-modified inorganic particles was used, based on 100 parts by weight of the base polymer powder, in Example 1. The content of fine powder having a particle size of about 150 μm or less in the superabsorbent polymer was less than about 2% by weight.

Comparative Example 1: Preparation of Superabsorbent Polymer

A superabsorbent polymer was prepared in the same manner as in Example 1, except that the surface-modified inorganic particles were not used in Example 1.

Comparative Example 2: Preparation of Superabsorbent Polymer 0.1 part by weight Aerosil 200 (Evonik) was added to and mixed with 100 parts by weight of the superabsorbent polymer prepared in Comparative Example 1.

Comparative Example 3: Preparation of Superabsorbent Polymer 0.3 part by weight Aerosil 200 (Evonik) was added to and mixed with 100 parts by weight of the superabsorbent polymer prepared in Comparative Example 1.

Experimental Example: Test of Physical Properties of Superabsorbent Polymer

Portions of the superabsorbent polymers prepared in Example 1, Example 2, Comparative Example 2, and Comparative Example 3 were taken and classified for 10 minutes using a testing sieve having a mesh size of #100 to remove dust from the superabsorbent polymers (Dedusting process).

Physical properties of the superabsorbent polymer before and after the dedusting process were measured by the following method and given in Table 1.

(1) Centrifuge Retention Capacity (CRC)

Centrifuge retention capacity (CRC) by absorbency under no load was measured for the superabsorbent polymers according to EDANA (European Disposables and Nonwovens Association) WSP 241.2.

In detail, the polymer W0(g) (about 2.0 g) was uniformly placed into a nonwoven-fabric-made bag, followed by sealing. Then, the bag was immersed at room temperature in a physiological saline solution which is 0.9% by weight of sodium chloride aqueous solution. After 30 minutes, the bag was drained at 250 G for 3 minutes with a centrifuge, and the weight W2(g) of the bag was then measured. Further, the same procedure was carried out using no polymer, and the resultant weight W1(g) was measured.

Thus, centrifuge retention capacity (CRC (g/g)) was calculated from these weights thus obtained according to the following Equation:

$$CRC(g/g)=\{[W2(g)-W1(g)]/W0(g)\}-1 \qquad \text{[Equation 1]}$$

wherein W0(g) is the initial weight (g) of the superabsorbent polymer,

W1(g) is the weight of the empty bag which is measured after immersing the bag in the physiological saline solution at room temperature for 30 minutes and draining water off at 250 G for 3 minutes with a centrifuge, and W2(g) is the weight of the bag including the superabsorbent polymer, which is measured after immersing the bag including the superabsorbent polymer in the physiological saline solution at room temperature for 30 minutes and draining water off at 250 G for 3 minutes with a centrifuge.

(2) Absorbency Under Pressure (AUP)

Absorbency under pressure (AUP) was measured for the superabsorbent polymers according to EDANA (European Disposables and Nonwovens Association) WSP 242.2.

First, a 400 mesh stainless steel net was installed in the bottom of the plastic cylinder having the internal diameter of 60 mm. The superabsorbent polymers W0(g) (0.90 g), of which absorbency under pressure was intended to be measured, was uniformly scattered on the steel net at room temperature and the humidity of 50%, and a piston which may provide a load of 4.83 kPa (0.7 psi) uniformly was put thereon, in which the external diameter of the piston was slightly smaller than 60 mm, there was no gab between the internal wall of the cylinder and the piston, and the jig-jog of the cylinder was not interrupted. The weight W3(g) of the apparatus thus prepared was measured.

After putting a glass filter having a diameter of 90 mm and a thickness of 5 mm in a petri dish having a diameter of 150 mm, a physiological saline solution (0.9% by weight of sodium chloride aqueous solution) was poured in the dish until the surface level became equal to the upper surface of the glass filter. A sheet of filter paper having a diameter of 90 mm was put on the glass filter.

Subsequently, the prepared measuring apparatus was put on the filter paper, and the superabsorbent polymer in the apparatus was allowed to be swollen by the physiological saline solution under the load. After 1 hr, the weight W4(g) of the apparatus including the swollen superabsorbent polymer was measured.

The weights thus obtained were used to calculate absorbency under pressure according to the following Equation 2:

$$AUP(g/g)=[W4(g)-W3(g)]/W0(g) \quad \text{[Equation 2]}$$

wherein W0(g) is the initial weight (g) of the superabsorbent polymer,

W3(g) is the total weight of the superabsorbent polymer and an apparatus capable of providing a load for the superabsorbent polymer, and W4(g) is the total weight of the superabsorbent polymer and the apparatus capable of providing a load for the superabsorbent polymer, which are measured after immersing the superabsorbent polymer in the physiological saline solution under a load of about 0.7 psi for 1 hour.

(3) Gel Bed Permeability (GBP)

The free swell gel bed permeability (GBP) of the superabsorbent polymer for the physiological saline solution was measured according to a method described in Patent Application No. 2014-7018005.

In detail, to measure free swell GBP, an apparatus shown in FIGS. 1 to 3 was used. First, a plunger 536, with a weight 548 seated thereon, was placed in an empty sample container 530 and the height from the top of the weight 548 to the bottom of the sample container 530 was measured using a suitable gauge accurate to 0.01 mm. The force the thickness gauge applies during measurement was controlled to less than about 0.74 N.

Meanwhile, a superabsorbent polymer to be tested for GBP was prepared from superabsorbent polymers which were prescreened through a US standard 30 mesh screen and retained on a US standard 50 mesh screen. As a result, a superabsorbent polymer having a particle size of about 300 μm to about 600 μm was prepared.

Approximately 2.0 g of the superabsorbent polymer thus classified was placed in the sample container 530 and spread out evenly on the bottom of the sample container. Subsequently, the container without the plunger 536 and weight 548 therein was then submerged for about 60 minutes in the physiological saline solution which is 0.9% by weight of sodium chloride aqueous solution to swell the superabsorbent polymer under no restraining load. In this regard, the sample container 530 was set on a mesh located in the liquid reservoir so that the sample container 530 was raised slightly above the bottom of the liquid reservoir. The mesh did not inhibit the flow of the physiological saline solution into the sample container 530. Also, depth of the physiological saline solution during saturation was controlled so that the surface within the sample container was defined solely by the swollen superabsorbent polymer, rather than the physiological saline solution.

At the end of this period, the plunger 536 and weight 548 assembly was placed on the swollen superabsorbent polymer 568 in the sample container 530 and then the sample container 530, plunger 536, weight 548, and swollen superabsorbent polymer 568 were removed from the solution. After removal and before being measured, the sample container 530, plunger 536, weight 548, and swollen superabsorbent polymer 568 were to remain at rest for about 30 seconds on a suitable flat, large grid non-deformable plate of uniform thickness. The height from the top of the weight 548 to the bottom of the sample container 530 was measured using the same thickness gauge used previously. The height measurement of the device where the plunger 536 and the weight 548 were placed in the empty sample container 530 was subtracted from the height measurement of the device including the swollen superabsorbent polymer 568 to obtain the thickness or height "H" of the swollen superabsorbent polymer.

The GBP measurement was initiated by delivering a flow of the physiological saline solution (0.9% by weight of sodium chloride aqueous solution) into the sample container 530 with the swollen superabsorbent polymer 568, plunger 536, and weight 548 inside. The flow rate of the physiological saline solution into the sample container 530 was adjusted to cause saline solution to overflow the top of the cylinder 534, resulting in a consistent head pressure equal to the height of the sample container 530. The quantity of solution passing through the swollen superabsorbent polymer 568 versus time was measured gravimetrically using the scale 602 and beaker 603. Data points from the scale 602 were collected every second for at least sixty seconds once the overflow had begun. The flow rate, Q through the swollen superabsorbent polymer 568 was determined in units of g/sec by a linear least-square fit of fluid (g) passing through the swollen superabsorbent polymer 568 versus time (sec).

Data thus obtained were used to calculate GBP (cm$^2$) according to the following Equation 3:

$$K=[Q*H*\mu]/[A*\rho*P] \quad \text{[Equation 3]}$$

wherein K is a gel bed permeability (cm$^2$),

Q is a flow rate (g/sec),

H is a height of the swollen superabsorbent polymer (cm),

μ is a liquid viscosity (P) (approximately 1 cP for the physiological saline solution used in this test), A is a cross-sectional area for liquid flow (28.27 cm² for the sample container used in this test), ρ is a liquid density (g/cm³) (approximately 1 g/cm³ for the physiological saline solution used in this test) and P is a hydrostatic pressure (dyne/cm²) (normally approximately 7,797 dyne/cm²).

The hydrostatic pressure was calculated from P=ρ*g*h, wherein p is a liquid density (g/cm³), g is a gravitational acceleration (nominally 981 cm/sec²), and h is a fluid height (e.g., 7.95 cm for the GBP test described herein).

At least two samples were tested, and a mean value of the results was used to determine the free swell GBP of the superabsorbent polymer. The unit was converted to darcy (1 darcy=0.98692×10⁻⁸ cm²), and given in Table 1.

534: Cylinder
534a: Region with outer diameter of 66 mm
536: Plunger
538: Shaft
540: O-ring
544, 554, 560: Hole
548: Annular weight
548a: Thru-bore
550: Plunger head
562: Shaft hole
564: 100 Mesh stainless steel cloth screen
566: 400 Mesh stainless steel cloth screen
568: Sample
600: Weir

TABLE 1

|  | Kind of inorganic particles (Content) | Before dedusting process (After surface crosslinking) | | | After dedusting process | | |
|---|---|---|---|---|---|---|---|
|  |  | CRC (g/g) | AUP (g/g) | GBP (darcy) | CRC (g/g) | AUP (g/g) | GBP (darcy) |
| Example 1 | Surface-modified inorganic particles of Preparation Example 1 (0.1 part by weight, based on 100 parts by weight of base polymer powder) | 34.6 | 23.3 | 11 | 34.3 | 23.5 | 9 |
| Example 2 | Surface-modified inorganic particles of Preparation Example 1 (0.3 parts by weight, based on 100 parts by weight of base polymer powder) | 32.6 | 21.6 | 41 | 32.4 | 22.2 | 45 |
| Comparative Example 1 | — | 34.5 | 22.7 | 3 | — | — | — |
| Comparative Example 2 | Aerosil 200 (0.1 part by weight, based on 100 parts by weight of superabsorbent polymer) | 35.1 | 21.0 | 8 | 34.1 | 21.6 | 4 |
| Comparative Example 3 | Aerosil 200 (0.3 parts by weight, based on 100 parts by weight of superabsorbent polymer) | 34.6 | 16.7 | 48 | 33.4 | 17.6 | 31 |

Referring to Table 1, the superabsorbent polymer according to an embodiment of the present invention was found to have excellent centrifuge retention capacity, absorbency under pressure, and permeability. In contrast, when any one physical property of centrifuge retention capacity, absorbency under pressure, and permeability of the superabsorbent polymers of Comparative Examples 1 to 3 was excellent, at least one of the other physical properties were poor.

Further, the superabsorbent polymers of Examples 1 and 2 maintained excellent physical properties because the inorganic particles did not break away therefrom even after the dedusting process, whereas the physical properties of the superabsorbent polymers of Comparative Examples 2 and 3 were deteriorated.

Accordingly, since the superabsorbent polymers according to an embodiment of the present invention have the surface crosslinking structure, their physical properties may be improved and deterioration in the physical properties may be minimized during the preparation and transportation of the superabsorbent polymers.

REFERENCE NUMERALS

500: GBP measuring apparatus
528: Test apparatus assembly
530: Sample container
601: Collection device
602: Scale
603: Beaker
604: Metering pump

The invention claimed is:

1. A method of preparing the superabsorbent polymer, the method comprising:
   polymerizing water-soluble ethylene-based unsaturated monomers in the presence of an internal crosslinking agent to form a hydrogel polymer, wherein the water-soluble ethylene-based unsaturated monomers have acidic groups which are at least partially neutralized;
   drying, pulverizing, and classifying the hydrogel polymer to form a base polymer powder; and
   crosslinking the surface of the base polymer powder in the presence of a surface crosslinking agent and surface-modified inorganic particles including surfaces modified with one or more functional groups selected from the group consisting of an epoxy group, a hydroxy group, an isocyanate group, and an amine group to form a surface crosslinking layer.

2. The method of claim 1, further comprising the step of modifying the surface of the inorganic particles with a modifier represented by the following Chemical Formula 1 to prepare surface-modified inorganic particles:

[Chemical Formula 1]

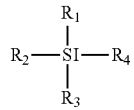

wherein $R_1$ to $R_3$ are each independently an alkyl group having 1 to 10 carbon atoms, an alkoxy group having 1 to 10 carbon atoms, or halogen, and at least one of them is not an alkyl group, and $R_4$ is a substituent having 2 to 10 carbon atoms, which has one or more functional groups selected from the group consisting of an epoxy group, a hydroxy group, an isocyanate group, and an amine group.

3. The method of claim 1, wherein the surface-modified inorganic particles are used in an amount of 0.01 to 10 parts by weight, based on 100 parts by weight of the base polymer powder.

\* \* \* \* \*